United States Patent [19]

Mioque et al.

[11] Patent Number: 4,974,245

[45] Date of Patent: Nov. 27, 1990

[54] SYSTEM FOR THE ASSEMBLY OF A METAL JOINING PIECE AND A HIGH PRESSURE COMPOSITE MATERIAL TUBE NOTABLY APPLICATIONS FOR EQUIPMENT USED IN THE OIL INDUSTRY

[75] Inventors: Jean-Yves Mioque, St Etienne; Bernard Montaron, St Priest en Jarez; Anne Lefevre, St Etienne, all of France

[73] Assignee: Dowell Schlumberger Incorporated, Tulsa, Okla.

[21] Appl. No.: 111,841

[22] Filed: Oct. 21, 1987

[30] Foreign Application Priority Data

Oct. 24, 1986 [FR] France ................................ 86 14949
Jun. 2, 1987 [FR] France ................................ 87 07722

[51] Int. Cl.$^5$ ............................................ G01N 23/06
[52] U.S. Cl. ........................................ 378/54; 378/51; 285/149; 285/93; 250/356.1; 250/432 R
[58] Field of Search ............... 378/51, 53, 54, 59, 378/47; 250/343, 356.1, 357.1, 432 R; 285/93, 144, 239

[56] References Cited

U.S. PATENT DOCUMENTS

| | | | |
|---|---|---|---|
| 3,049,617 | 8/1962 | Fabian, Jr. et al. | 250/356.1 |
| 3,613,736 | 10/1971 | Kuwabara | 285/239 |
| 4,200,792 | 4/1980 | Fanger et al. | 378/53 |
| 4,225,158 | 9/1980 | Puechary | 285/239 |
| 4,265,951 | 5/1981 | Yates et al. | 285/114 |
| 4,313,627 | 2/1982 | de Lange | 285/114 |
| 4,314,718 | 2/1982 | Broyles et al. | 285/114 |
| 4,428,602 | 1/1984 | Lambot et al. | 285/239 |
| 4,470,621 | 9/1984 | Irvine | 285/114 |
| 4,609,210 | 9/1986 | Torokvei et al. | 285/114 |

FOREIGN PATENT DOCUMENTS

| | | | |
|---|---|---|---|
| 0320362 | 2/1975 | Austria | 285/239 |
| 0767492 | 7/1971 | Belgium | 285/239 |
| 0037484 | 4/1978 | Japan | 250/356.1 |
| 0228151 | 12/1984 | Japan | 378/59 |

Primary Examiner—Janice A. Howell
Assistant Examiner—John C. Freeman
Attorney, Agent, or Firm—S. A. Littlefield

[57] ABSTRACT

Device to permanently link a metal joining piece and a composite material tube, to a tube subjected to static pressure up to 150 MPa. The assembly consists of a metal part constituting a sealing (8) and joining (7) piece with a collar (2), onto which the composite material (1) is attached. A tubular anti-abrasion and anti-corrosion (6) sleeve, flush-mounted in the metal joining piece and protected by a ring (9) at its end ensures total isolation of the composite/metal joint from corrosive fluids which may be flowing through the tube. In particular, the application of the device to oil industry sensors.

10 Claims, 3 Drawing Sheets

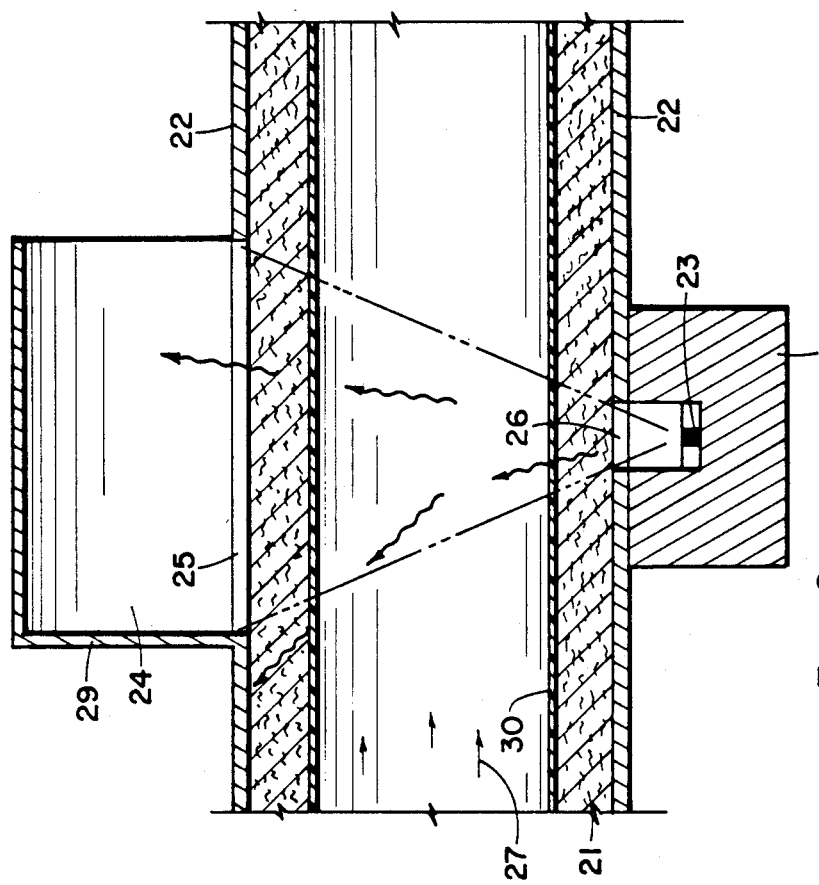
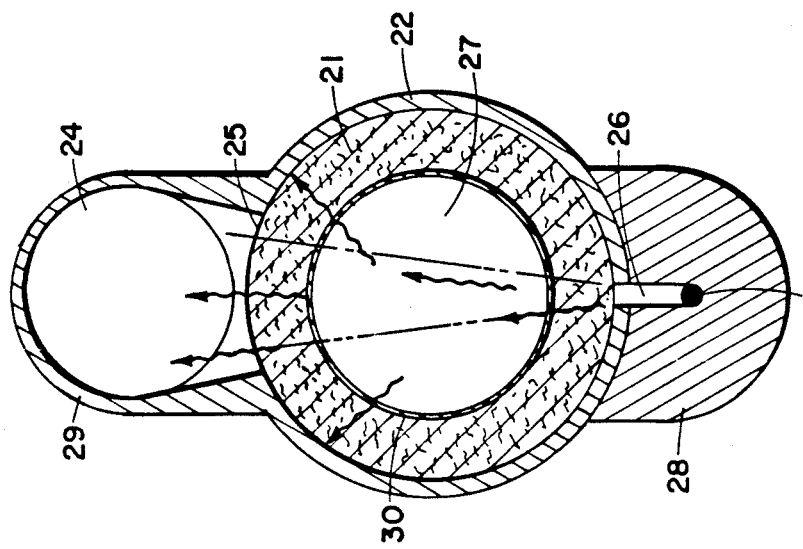

SYSTEM FOR THE ASSEMBLY OF A METAL JOINING PIECE AND A HIGH PRESSURE COMPOSITE MATERIAL TUBE NOTABLY APPLICATIONS FOR EQUIPMENT USED IN THE OIL INDUSTRY

BACKGROUND OF THE INVENTION

This invention concerns an assembly system for composite material and metal, making the use of composite materials for transportation of corrosive and/or abrasive fluids possible at static pressures of up to 150 MPa.

In particular, the invention facilitates insertion between metal tubes (through which a fluid under very high pressure is flowing) of a composite tube element which may be part of a sensor designed to measure various properties of the fluid (viscosity, flow-rate, density, etc.)

One of the problems recognized in the previous state of the art was the difficulty of realizing composite material/metal joints able to withstand very high pressures for long periods of time. The invention solves this problem.

One most important application is to sensors used in oil and oil-related industry, used, as is well-known, to measure the properties (viscosity, density, rheology, etc.) of fluids piped under very high pressure, which may be corrosive (acids) and/or highly abrasive (cement slurries).

Using the invention, a metal joining piece with a projecting collar at the end in contact with the composite material and a high pressure joining piece at the other end is placed between the composite material and the metal tube.

One of the invention's essential characteristics is the projecting collar (2) around which the various layers of composite material are placed in the accustomed manner, by winding.

The advantage of this structure is that normal winding of the composite material is made possible while, for the first time, resistance to tensile and torsional stresses occurring between the metal tube (and the metal joining piece) on the one hand, and the composite tube on the other, is ensured.

Thus, risk of distortion, leaks and fractures, which are common in attempts made in the previous state of the art, is eliminated.

Considering the working pressures, it is evident that this advantage is quite decisive.

Within oil and oil-related industry, the drawbacks of the previous state of the art have even more serious consequences (any interruption of work on a line involves serious risks bad well treatment, bad cement placement; with sometimes unsalvageable consequences).

The invention will be described in conjunction with reference to the appended drawing figures illustrating preferred embodiments of the invention and forming a part of this Specification and in which.

Figure 3:
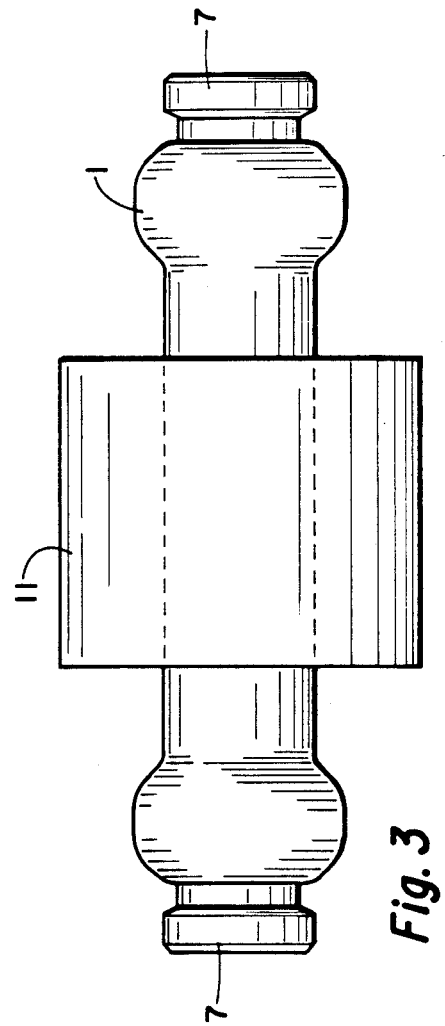
FIGS. 3 and 4 are elevational views of the tubing of this invention shown with and without an associated measuring device, respectively and, FIGS. 5 and 6 are cross-sectional views of the tubing and measuring device shown in FIG. 3.

References are as follows:

1. Wound composite material
2. Collar on metal joining piece
3. Metal joining piece
4. Circumferential fibers of the composite material
5. Longitudinal fibers of the composite material
P. Pressure exerted by the pumped fluid inside the tube
S. Tube section
F. Forces of longitudinal tension due to pressure
R. Radius of collar
AB. Angles of the oblique planes of the collar
6. Anti-abrasion/anti-corrosion sleeve
7. "Weco" type assembly system with a high-pressure metal tube not shown
8. High-pressure seal
9. Protective ring
10. O-rings FIG. 3 is a drawing of a sensor (11) mounted on the tube. The sensor measures the properties of the fluid travelling through the tube, taking measurements through the tube's (1) composite material walls.

Figure 4:
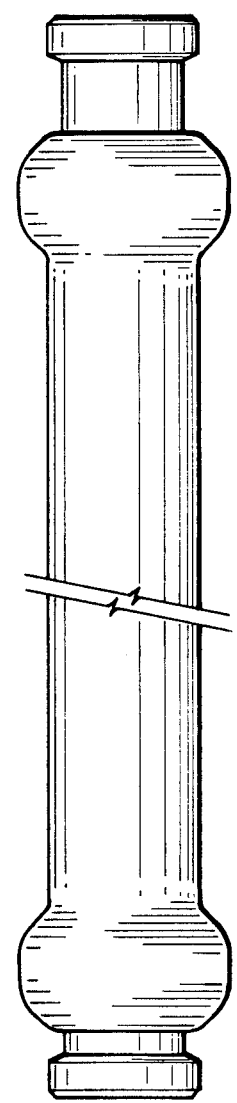

FIG. 4 shows a very high pressure tube of composite material which can be joined at both ends using the invention.

Figure 1:
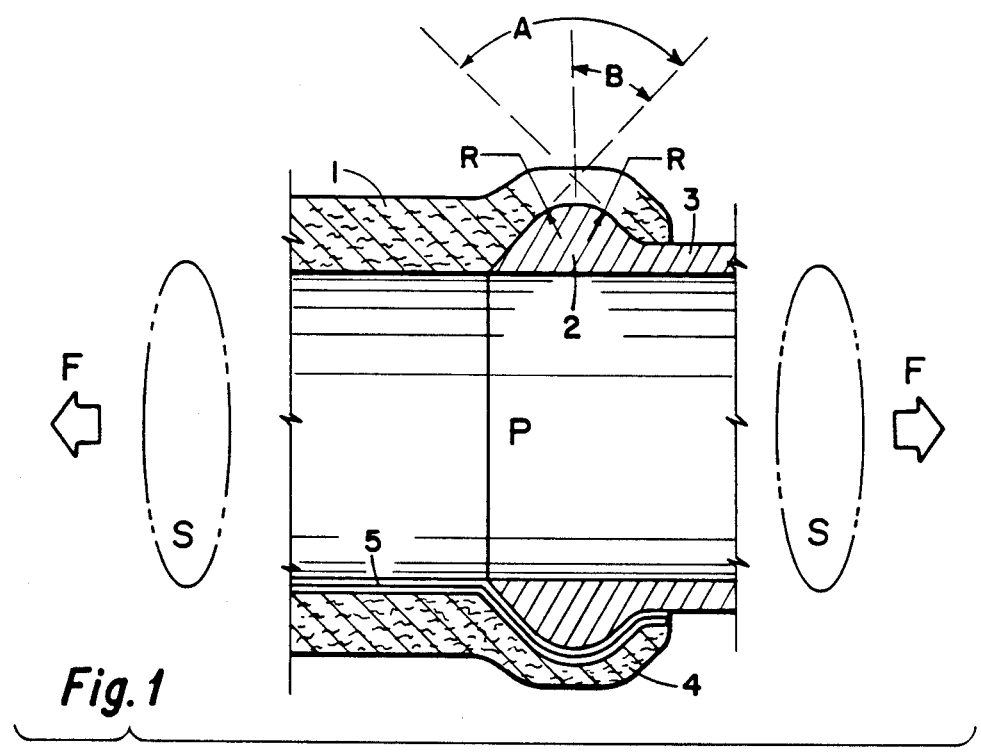
FIGS. 1 and 2 are cross-sectional views of a joining piece in accordance with the invention.

FIG. 1 shows the working principle of the invention in detail.

When a very high pressure P is applied inside the tube, it creates a strong tensile force $F = P \times S$ within the material constituting the tube.

The longitudinal fibers (5) of the composite material partially absorb this force. In the joint zone of the composite tube and the metal joining piece (3), shearing forces at the interface of the two materials reach values such that no adhesive suffices to keep the assembly together.

It is in this context that the assemblies of the previous state of the art are fragile. Using the invention discussed here, the composite material tube is wound around a projecting collar (2) on the metal joining piece.

When a pulling force is exerted on the tube, any slippage should be absorbed by an increase in diameter of some of the turns in the layer of circumferential fibers (4) in the composite material.

These fibers consist of a material with very high Young's modulus, as is notably the case in glass, carbon or aramid fibers. It is therefore very difficult, if not impossible, to cause the assembly to slip, whether by pulling apart or by compressing. This is due to the shape of the collar (2) which has two oblique planes with angles A and B.

To avoid breaking the longitudinal fibers by incipient fracture, care will be taken to select appropriate radii R for the collar.

Collar profile may be chosen in various ways, but it should preferably have a shape which causes diameter changes to be as "gentle" as possible.

In another preferred method of winding, composite material fibers are wound in two symmetrical spirals (one left-handed, the other right-handed), with the fiber angle, measured in relation to the tube axis, being from 50° to 60°. It is well-known that a tube consisting of spirally wound fibers wound at an angle of approximately Arc tan (2), 54.73°, is practically unexpandable through the effect of pressure forces.

Finally, it is possible to envisage the configuration of the invention as a combination of more than 2 layers of fibers with winding angles selected from the examples given.

Figure 2:
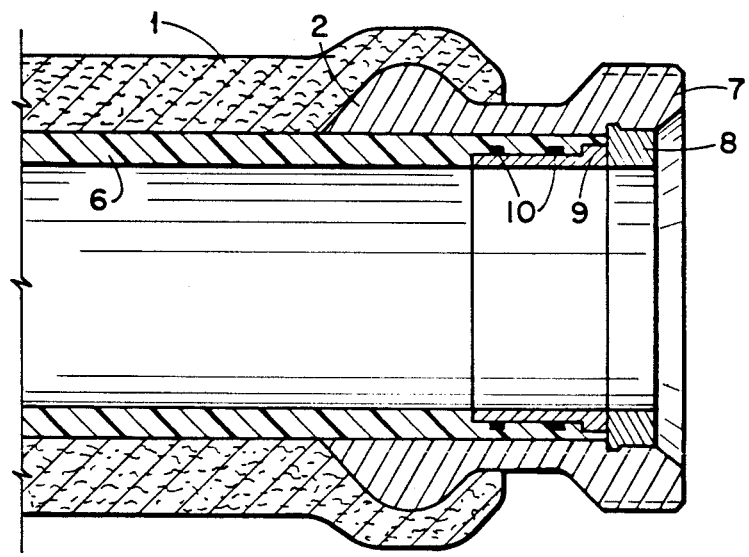

FIG. 2 is a drawing of the invention. A sleeve 6, made of a material (notably polyurethane or polytetrafluorethylene) which is resistant to (corrosive or abrasive) fluids pumped, protects the composite material from chemical attack. In fact, it is known that resins linking the material's reinforcing fibers can be dissolved by certain fluids and that glass fibers are attacked by hydrofluoric acid.

The sleeve 6 can be used advantageously when manufacturing the tube. It can be used as a guide when winding the composite material over the metal joining piece 2.

The metal part 9 attached to the seal 8 enables the end of the sleeve 6 to be protected against abrasion. The O-rings 10 provide a complete seal, so preventing penetration of aggressive fluids between part 9 and the sleeve 6, through the effect of pressure.

In this example, the end 7 of a "Weco" type female high-pressure joint has been depicted. The WECO assembly system is well-known, especially in oil and oil-related industry. It could, however, be replaced by any other system, known to those skilled in the art, which would be capable of resisting the very high pressures mentioned here.

FIG. 3 shows the application of the invention to the implementation of sensors which can be attached to high-pressure lines. In this application mode, the sensor (11) measures one or more properties of the fluid travelling through the composite tube 1. The sensor may be a flow meter, densitometer or conductivity measuring sensor of known type not requiring detailed description here.

FIG. 3 shows the application of the invention to the implementation of sensors which can be attached to high-pressure lines. In this application mode, the sensor (11) measures one or more properties of the fluid travelling through the composite tube 1. The sensor may be a flow meter, densitometer or conductivity measuring sensor of known type not requiring detailed description here.

Finally, FIG. 4 shows a very high pressure pipe with a male and a female (respectively) "Weco" type joint at each end, joined to the composite material tube using the invention.

The interest of using polymer-based composite materials for high-pressure lines lies above all in the great weight-saving, which makes for easier handling and the possibility of carrying a larger number of pipes per lorry. For industry, notably oil and oil-related industry, this advantage is of utmost importance, especially in the oilfield and offshore.

One particularly interesting application is the non-intrusive measurement of the density of a fluid travelling through a tube. One frequently-used technique consists of measuring the absorption, by the said fluid, of photon radiation emitted by a source placed diametrically opposite the detector. Radiation absorption is related to the fluid density by an exponential law. After the device has been calibrated, the signal picked up by the detector can be converted directly into density.

Use of this technique in the industrial and oil-industry context, particularly when high pressures are being used, requires that the device be installed on relatively thick tubes, generally of metal, which results in much of the radiation emitted from the source being absorbed by the tube; considering this additional absorption, the radiation level imposed by detector sensitivity requires the use of highly active photon sources. This considerably complicates on the one hand the legislation and administrative channels required when using radioactive sources and, on the other, makes use of heavy and bulky protective shielding necessary. The invention discussed here uses a tube of composite material as part of the standard density measurement device. This material has the property of absorbing considerably less of the radiation in question than steels and, more generally, metals, which makes it possible to considerably reduce the radiation source activity while retaining an identical detection signal. Consequently, protective shielding around the source and so the weight and size of the assembly are also reduced. Moreover, composite materials have mechanical and chemical properties which are comparable with or superior to those of metals, so making use of this technique possible in a large number of industrial applications and hostile environments. The above-mentioned properties of composite materials have been known for around ten years. However, it has not, in that time, seemed possible to use them within the field of very high pressure devices using a permanent radiation source. Also, the industry did not have any reliable means of making metal/composite joints capable of resisting these very high pressures. This includes oil field applications. Experiment has shown that, in fact, use of these materials is compatible with the application envisaged, particularly as a result of the assemblies described above.

FIG. 5 shows a section, in a plane perpendicular to the tube, through an experimental gamma ray device.

FIG. 6 shows the longitudinal section of the same device.

The same numerical references designate the same elements in both these figures.

Element 21 is the composite material tube; it is complete, i.e., must not be machined, in order to respect standards concerning the use of high pressures. Its diameter, length and wall thickness are defined depending on the circumstances in which the densitometer is used. The fluid 27, the density of which is to be measured, flows through the tube. Depending on the individual application, and especially depending on the fluid pumped, a protective covering 30 inside the tube may be required, particularly if the fluid is an acid. The covering should be of a material of the polyurethane or polytetrafluorethylene type, or analogous, in order to conserve good anti-abrasion properties, particularly in applications using cement slurries. Element 28 is the photon source support, the source in this case being of the chemical radioactive type. This element is made of lead contained in a support which is mechanically solid and well attached to the shielding 22 which encircles the tube 21. The lead is present to absorb the radiation emitted by the source 23 in directions other than those defined by the collimator window 26, thus limiting doses of escaping radiation around the device to the values defined by radioprotection standards. In this case, the source 23 is a radioisotope the nature and activity of which are defined as a function of the densitometer operating conditions (tube dimensions, detector type, type of fluid flowing through the tube). Depending on requirements, a source obscuring system may be considered. Element 22 is the shielding encircling the composite tube. The shielding consists of a substance which greatly absorbs high energy photons (100 to 1000 KeV), such as steel, lead, tungsten, tantalum or a combination of these materials. It is designed to attenuate those photons which, after interacting with an atom in the fluid or tube, are diffused in directions other than their original direction.

The thickness of the shielding depends on the material of which it consists, source activity and device dimensions, and should be defined taking the standards defined by radioprotection bodies into account. A shield, shown at number 29 and consisting of the same materials or a combination of them, also surrounds the detector 24. The two elements 22 and 29 can be either all in one part or two individual parts mechanically joined (e.g., by welding) to form one non-separable assembly. Element 29 is also a support for the detector 24. Element 24, which is not shown, is a standard radiation detector of the ionizing (ionizing chamber, proportional counter, Geiger-Mueller counter), scintillation or semiconductor type. Choice of detector depends on the circumstances in which the densitometer is used. The detector includes in the electronic circuitry required for operation. Elements 26 and 25 are, respectively, the collimator windows for source and detector. Source collimation 26 is defined by an aperture in the support 28 and the shield cylinder 22. Geometry is adapted to the various densitometer element dimensions and depends on the desired degree of collimation. On the detector side, the collimator window 25 also consists of a rectangular aperture in the shield cylinder 22; width, shown in FIG. 5 and length, shown in FIG. 6, of this window depend on the radiation beam angle defined by source collimation 26, detector size and tube dimensions. The angular limits of the "exploitable" photon beam emitted by the source are shown in FIGS. 5 and 6, as is the possible course of some photons (symbolized by waved arrows) in the various cases envisaged.

The principles of operation of this device are identical to those of existing radiation densimeters. The photons emitted by source 23 and collimated through window 26 firstly cross the first composite tube wall, then the fluid flowing through the tube and finally the second tube wall, before entering the detector assembly.

During this course, each photon has a certain probability of undergoing one or more interactions with the atoms in the material it is passing through; this probability is all the higher, the greater the density of the material considered. The result of these interactions is either absorption of the photon, which then has an energy value slightly less than its initial one and travels in a different direction from the original one [Compton diffusion]. The principle of densitometer measurement relies on detection of those photons which pass between the source and the detector without interacting on the way. It is obvious that the number of photons which do this varies in inverse proportion to the density of the materials crossed and also with the distance travelled through each material. The materials crossed in the case of a radiation-based densitometer are the tube and the fluid the density measurement of which is required. It can therefore be understood why it is essential to reduce the effect of tube wall photon absorption. This is the aspect which is the major advantage of the invention. As a result of this use of composite material for the tube, radiation densimeters with considerably reduced source activity, which retain similar or superior performance to standard densimeters, can be used. This is because composite material density is 4 times less than the density of steel, while composite has mechanical properties comparable or superior to those of steel at wall thicknesses increased by a factor of 2 compared with classical steel tubes. Amongst the advantages of the invention compared with a classical system, over and above that of reducing source activity, the following points should be mentioned:

total device weight is reduced, as composite is more abrasion-resistant than steel, it is perfectly suited to the use of fluids as abrasive as cement slurries or fluids carrying propping agents (sand, stone chips, etc.), corrosion and rust problems encountered in steel tubes are eliminated, which, apart from better service life results, also yields the advantage of better quality control and better wall thickness invariability, thus a more stable geometry, which is an important point when seeking high precision of measurements.

Of course, application of the invention is not limited to the oil industry, and covers other known fields in which radiation densimeters, as well as other sensors such as flow meters, etc., are used. The invention is sure to be of great usefulness in all fields in which a tubular element (sensor, etc.) is applied to a tubular metal line, and where the composite material having previously been impossible due to the absence of suitable metal/composite joints, especially in high pressure applications).

We claim:

1. An assembly comprising a composite material cylindrically symmetrical part and a metal part, capable of resisting very high internal pressures, characterized in that a first end of the composite material cylindrically symmetrical part having a first internal diameter at least partially encloses and covers a cylindrical-symmetrical metal joining piece at one end including a collar with an internal diameter equal to said first internal diameter, a section of which has a generally trapezoidal shape in a place of a longitudinal axis of symmetry, around which reinforcing fibers of the composite material cylindrically symmetrical part are wound, further characterized in that a second end of the cylindrical-symmetrical metal joining piece comprises a high pressure joint including means for attachment to a second metal part.

2. The assembly in accordance with claim 1, characterized in that the composite material cylindrically symmetrical part and the cylindrical-symmetrical metal joining piece are capable of resisting very high pressures, and in that the second metal part comprises one of a very high pressure tube and a very high pressure plug.

3. The assembly in accordance with claim 1 characterized in that the composite material cylindrically symmetrical at an interface with the cylindrical-symmetrical metal joining piece consists of at least one longitudinal layer of reinforcing fibers, lying in a direction parallel to the longitudinal axis of symmetry and at least one circumferential layer of reinforcing fibers, wound in generally circular turns placed in directions substantially perpendicular to the longitudinal axis of symmetry.

4. The assembly in accordance with claim 1, characterized in that an inside wall of the composite material cylindrically symmetrical part is fitted with a coaxial tube which protects the composite material cylindrical symmetrical part from any aggressive fluids which may be pumped through the composite material cylindrically symmetrical part, particularly acids and abrasive fluids.

5. The assembly in accordance with claim 4, characterized in that the coaxial tube is a material selected from a group consisting of polyurethane and polytetrafluorethylene.

6. The assembly in accordance with claim 1 characterized in that the composite material cylindrically symmetrical part comprises a fiber-linking resin reinforcing fibers selected from a group consisting of glass, carbon and aramid fibers.

7. The assembly in accordance with claim 1 wherein a fluid flows through said composite material cylindrically symmetrical part and wherein said assembly further comprises sensor means attached to said composite material cylindrical symmetrical part, wherein said sensor means measures certain properties of said fluid.

8. The assembly of claim 1 further including a densitometer comprising an energetic photon source and a detector which measures photon absorption by a fluid flowing through a tube, the assembly being enclosed in an area of photon diffusion, by a metal cylinder which greatly absorbs the photons emitted by the energetic photon source and has a window for the source and a window for the detector.

9. The assembly in accordance with claim 8 wherein the energetic photon source emits, by radioactivity, gamma photons, and has an activity of less than about 25 mCi, and in that the detector is of one of the following types: ionization, scintillation or semiconductor.

10. The assembly in accordance with claim 8 wherein the energetic photon source emits x-ray photons by means of an artificial device of an x-ray tube or x-ray laser type and in that the detector is of one of the following types: ionization, scintillation or semiconductor.

* * * * *